United States Patent [19]

Scheuble et al.

[11] 4,394,172

[45] Jul. 19, 1983

[54] NON-DUSTING AND FAST-WETTING IMPRESSION MATERIAL AND METHOD OF PREPARING SAME

[75] Inventors: Max Scheuble, Zurich; Paul Munsch, Oberhasli, both of Switzerland

[73] Assignee: Dentsply Research & Development Corp., Del.

[21] Appl. No.: 293,143

[22] Filed: Aug. 17, 1981

Related U.S. Application Data

[63] Continuation-in-part of Ser. No. 181,417, Aug. 26, 1980, abandoned.

[51] Int. Cl.$^3$ .......................... A61C 9/00; C08L 1/08; C08L 5/04
[52] U.S. Cl. ........................... 106/38.5 D; 106/193 J; 106/209; 106/308 C; 106/308 Q
[58] Field of Search ..................... 106/209, 35, 308 Q, 106/308 C, 38.5 D, 193 J; 433/214; 252/88; 404/76

[56] References Cited

U.S. PATENT DOCUMENTS

| Re. 23,700 | 8/1953 | Lochridge | 106/38.5 R |
|---|---|---|---|
| Re. 29,295 | 7/1977 | Steel et al. | 106/308 C |
| 2,345,255 | 3/1944 | Gross | 106/209 |
| 2,390,137 | 12/1945 | Vallandigham | 106/209 |
| 2,397,145 | 3/1946 | Joy et al. | 106/209 |
| 2,422,497 | 6/1947 | Noyes | 106/209 |
| 2,623,808 | 12/1952 | Meyer | 106/209 |
| 2,628,153 | 2/1953 | Noyes et al. | 106/209 |
| 2,631,081 | 3/1953 | Noyes et al. | 106/209 |
| 2,631,082 | 3/1953 | Noyes et al. | 106/209 |
| 2,678,280 | 5/1954 | Noyes et al. | 106/209 |
| 2,733,156 | 1/1956 | Cornell et al. | 106/38.5 D |
| 2,816,040 | 12/1957 | Rabchuk | 106/209 |
| 2,844,486 | 7/1958 | Lamarr | 106/308 Q |
| 2,878,129 | 3/1959 | Rabehuk | 106/38.4 |
| 3,246,998 | 4/1966 | Higachi et al. | 433/214 |
| 3,291,618 | 12/1966 | Morrell | 106/209 |
| 3,620,778 | 11/1971 | Morrell | 524/28 |
| 3,966,488 | 6/1976 | Langenfelder et al. | 106/308 Q |
| 4,136,050 | 1/1979 | Brehm | 252/88 |
| 4,344,766 | 8/1982 | Lahrs et al. | 8/524 |

FOREIGN PATENT DOCUMENTS 530730 9/1956 Canada .
727520 4/1955 United Kingdom .

OTHER PUBLICATIONS

Woody, R. D. et al., JADA 94, 501, 1977.

*Primary Examiner*—Allan Lieberman
*Attorney, Agent, or Firm*—Anthony J. DeLaurentis; Edward J. Hanson, Jr.

[57] ABSTRACT

A non-dusting and fast-wetting powdered impression material is prepared by coating at least a portion of the powder components of an otherwise conventional impression material with a surface coating agent prior to mixing with water.

6 Claims, No Drawings

NON-DUSTING AND FAST-WETTING IMPRESSION MATERIAL AND METHOD OF PREPARING SAME

This application is a continuation-in-part of Ser. No. 181,417, filed Aug. 26, 1980, and now abandoned.

BACKGROUND OF THE INVENTION

This invention relates to impression materials, particularly for use in dental applications, which are formed by mixing a powdered material with water, as for example alginate impression materials or alginate substitute materials, i.e., those in which the alginic acid salt component is replaced by a substitute polymer, for example, carboxymethyl cellulose, xanthan gum, and the like.

Alginate impression and alginate substitute materials are known and have been used successfully for many years in the dental arts. See, for example, U.S. Pat. Nos. 2,345,255 to Gross; 2,390,137 to Vallandigham; 2,397,145 to vanBuren Joy; 2,422,497 to Noyes; 2,878,129 to Rabchuck; 3,246,998 to Higashi et al; Reissue 23,700 to Lockridge; and 2,733,156 to Cornell; the disclosures of these patents relevant to the preparation of conventional alginate and alginate substitute impression materials being incorporated herein by reference.

The use of such impression materials generally involves the proper measuring and then mixing of certain powdered constituents or components of the impression material (referred to hereinafter as the powdered components), with water or a substitute liquid, proper measuring of the powdered and liquid components being essential to obtaining satisfactory physical properties. Prior to mixing the powdered and liquid components, it is common practice for the user to shake the container in which the various powdered components of the impression material are stored to fluff them. This fluffing is done to facilitate the measuring or proportioning of the powdered components, using a scoop or ladle which usually is provided with the container. Under such circumstances, however, when the top of the container is opened, some of the fluffed powder tends toward dusting, i.e., becoming airborne and floating out of the container. Dusting also tends to occur when the powdered components are mixed with water or a water substitute due, at least in part, to the difficulty with which the powdered components are wet by the water. In practice, the powdered components are placed in a flexible mixing bowl and water is added to it. The powdered components do not wet immediately and the bulk of the powder floats for a period of time on the surface of the water during mixing, thus permitting some dusting to occur. The dusting problem is further exaggerated because the harder one stirs the powdered components/water mix, the greater is the opportunity for a portion of the powder to become airborne.

This dusting, which occurs primarily when a portion of the filler in the powdered components separates from the remaining powdered components and becomes airborne upon mixing or shaking, or upon stirring with the liquid component of the impression material has become the cause of concern because of its potential health hazard. (Woody, R. D. et al, JADA 94, 501, 1977). According, it is a principal object of the present invention to reduce the dusting that occurs when the filler in the powdered components separates and becomes airborne upon mixing or shaking.

It is another object of the present invention to achieve easier wetting of the powdered components by water or a substitute liquid.

DESCRIPTION OF THE INVENTION

In accordance with the present invention, the greater ease and speed with which the powdered components are wet by water during mixing, the elimination of airborne particles of powder, and other objects and advantages are achieved when the constituent powdered particles, or at least a portion thereof, are coated with a minor amount of a surfactant/dispersing agent or compound which is readily and rapidly wet, dispersed or dissolved by the water or substitute liquid component of the impression material. This coating of the powdered particles causes the individual particles to be attracted to one another so that they do not easily become airborne, and permits the powder particles to be easily wet by the water or substitute liquid. Examples of substances which may be used to coat the powdered particles, are, for example, natural polymer dispersing agents such as xanthan gum, sodium polyalginate or potassium polyalginate, cellulose esters or ethers having ester or ether groups containing free hydroxy or carboxyl groups such as hydroxyethyl or hydroxymethyl cellulose, carboxyl methyl cellulose, synthetic ionic polymeric surfactants such as those which contain substantial amounts of units derived from alkylene oxides such as polyethylene glycol or polypropylene or polybutylene glycol or copolymers of them, including polymeric surfactants of which the Tween and Brij series produced by ICI Americas are examples, and other including, for example, block copolymers of polysiloxanes and polyethylene glycols. The coating agent need not necessarily be limited to polymers but may include monomeric substances, for example, polyols such as ethylene glycol, propylene glycol, alkanolamines such as triethanolamine, and compounds such as lauryl sulfate, sucrose butyrate, glycerol esters, and the like. Mixtures of the above coating agents also may be used. It should be evident, then, that a wide variety of coating agents may be employed, in varying dusting reducing, powder wetting enhancing amounts, usually from about 1-10% by weight based on the total weight of the powdered components, so long as the respective agent that is used adequately coats the powdered components, and is readily and quickly wet, dispersed or dissolved by the liquid component of the impression material to provide a composition wherein dusting is significantly reduced and the powdered components are significantly more rapidly wet upon mixing as compared to the same composition absent the coating agent.

The preferred composition of the invention has a Dust Index of less than about 100 using a Gelman Air Analyzer (See Example 4).

The invention will be more fully understood in conjunction with the following examples thereof, which examples merely are illustrative and should not be considered to be limitive of the materials and procedures employed in practicing the invention.

EXAMPLE 1

An alginate impression material was produced from the following components:

| Component | Parts by Weight |
|---|---|
| Sodium alginate | 14.0 |

| Component | Parts by Weight |
| --- | --- |
| Calcium sulfate | 17.4 |
| Tetrasodium pyrophosphate | 2.5 |
| Potassium titanium fluoride | 1.0 |
| Magnesium oxide | 2.6 |
| Diatomaceous earth (filler) | 57.8 |
| Polypropylene glycol (coating agent) | 4.7 |

The diatomaceous earth filler was wet with the polypropylene glycol coating agent before being admixed with the other powdered components. The entire mixture was blended in a ribbon blender. A 14 gram sample of the resulting mixture was placed in a mixing bowl mounted on an "Alginator" produced by Cadco Products. An appropriate quantity of water was then added to the bowl and the "Alginator" was caused to turn. A spatula was held in a fixed position in the turning mixture and it was observed that after 5 seconds the alginate powder was wet. It was also observed that there were no dust particles released upon stirring.

EXAMPLE 2

The procedures of Example 1 were repeated, except that potassium alginate was used in place of sodium alginate. A complete wetting of the alginate was noted within 5 seconds and no dusting was observed.

EXAMPLE 3

The procedure of Example 1 was repeated except that the polypropylene glycol (coating agent) was eliminated from the alginate powder formulation. In contrast with the results of Example 1, it was observed that it took the same alginate formulation, except for the omission of the surface coating agent, 10 seconds to be wet by the water. It was also observed that there was a great deal of "dusting".

EXAMPLE 4

In order to quantify the observation of dusting a standard container of alginate impression material powder was fluffed by turning and rotating the container for 20 seconds. Immediately the top was removed and the relative concentration of particles released from the surface were quantified using a Gelman Air Analyzer, a unit which is designed to measure particulate contaminates in industry. The air immediately above a container of the alginate formulation prepared in accordance with Example 1, i.e. having a coating agent present on the filler particles, was sampled and a particle content (Dust Index) of 6.5 micro grams per liter of air per minute was observed. This was much less than a particle content (Dust Index) of 215 micro grams per liter of air per minute measured for the same alginate impression material powder handled in the same manner, but not surface treated. Both the surface treated powder and that not treated, complied fully with the requirement of ADA Specification 18 for Alginate Impression Material.

Using the same procedure, additional dust-free alginate compositions were made using different coating agents. Successful coating agents, their "Dust Index", and chemical name are listed in the following Table:

| Trade Name | HLB Value | Chemical Name | "Dust Index" |
| --- | --- | --- | --- |
| Xanthan gum | | | 59 |
| Tween 20 | 16.7 | polyoxyethylene (20) sorbitan monolaurate | .14 |
| BRIJ 97 | 12.4 | polyoxyethylene (10) oleyl ether | 34 |
| SPAN 85 | 1.8 | Sorbitan trioleate | 37 |
| Propylene glycol | | | 44 |

These coating agents all are capable of providing useful alginate materials.

EXAMPLE 5

The procedure of Example 1 was repeated, except that the alginate impression material was produced from the following components:

| Component | Parts by Weight |
| --- | --- |
| Sodium alginate | 8.5 |
| Potassium alginate | 8.5 |
| Magnesium oxide | 3.0 |
| Magnesium carbonate | 4.0 |
| Potassium fluorotitanate | 4.1 |
| Calcium sulfate | 17.0 |
| Sodium fluoride | 0.5 |
| Sodium tripolyphosphate | 1.5 |
| Potassium diphosphate | 1.3 |
| Polypropylene glycol | 3.5 |
| Diatomaceous earth | 48.0 |

A complete wetting of the alginate impression material was noted within 5 seconds and no dusting was observed.

Although the present invention has been described in connection with preferred embodiments thereof, it is to be understood that modifications and variations may be resorted to, without departing from the spirit and scope thereof, as those skilled in the art will readily understand. Such modifications and variations are considered to be within the purview and scope of the appended claims.

What is claimed is:

1. In a dry powdered impression material comprising an alginic acid salt component and a filler component, wherein said material exhibits a tendency toward dusting in its dry powdered state, wherein said material is mixable with water to form an impression paste capable of setting to a solid, and wherein said material exhibits a further tendency toward dusting upon admixture with water, the improvement comprising a coating on at least a portion of the powdered components rendering said material substantially non-dusting in its dry powdered form and during admixture with water, said coating being readily and rapidly wet, dispersed or dissolved by water and present in an amount of from about 1–10% by weight based on the total weight of the dry powdered components.

2. The impression material of claim 1, wherein said coating agent is selected from the group consisting of natural polymer dispersing agents, cellulose ester and ethers having ester or ether groups containing free hydroxyl or carboxyl groups and synthetic nonionic polymeric surfactants.

3. The impression material of claim 1, wherein said coating agent is selected from the group consisting of xanthan gum, hydroxyethyl or hydroxymethyl cellulose, carboxy methyl cellulose, sodium polyalginate or potassium polyalginate, polyethylene glycol or polypropylene glycol or polybutylene glycol or copolymers thereof, ethylene glycol, propylene glycol, triethanolamine lauryl sulfate, sucrose butyrate, glycerol esters and mixtures thereof.

4. The impression material of claim 1 consisting essentially of the following components in admixture:

| Component | Parts by Weight |
|---|---|
| sodium alginate or potassium alginate | 14.0 |
| calcium sulfate | 17.4 |
| tetrasodium pyrophosphate | 2.5 |
| potassium titanium fluoride | 1.0 |
| magnesium oxide | 2.6 |
| diatomaceous earth | 57.8 |
| polypropylene glycol | 4.7, | wherein said diatomaceous earth had been coated with said polypropylene glycol prior to having been mixed with the remaining components.

5. The impression material of claim 1 consisting essentially of the following components in admixture:

| Component | Parts by Weight |
|---|---|
| sodium alginate | 8.5 |
| potassium alginate | 8.5 |
| magnesium oxide | 3.0 |
| magnesium carbonate | 4.0 |
| potassium fluorotitanate | 4.1 |
| calcium sulfate | 17.0 |
| sodium fluoride | 0.5 |
| sodium tripolyphosphate | 1.5 |
| potassium diphosphate | 1.3 |
| polypropylene glycol | 3.5 |
| diatomaceous earth | 48.0 | wherein said diatomaceous earth had been coated with said polypropylene glycol prior to having been mixed with the remaining components.

6. A method for controlling the dusting of a powdered impression material comprising coating at least a portion of the powder with from about 1–10% by weight, based on the total weight of the powdered components, of an agent which when dry renders the powder, in its dry powder form, relatively non-dusting.

* * * * *